United States Patent
Boyle et al.

(10) Patent No.: US 10,758,256 B2
(45) Date of Patent: Sep. 1, 2020

(54) ULTRASONIC ENDOVASCULAR CATHETER

(71) Applicant: C.R. Bard, Inc., Tempe, AZ (US)

(72) Inventors: Kevin Boyle, Scottsdale, AZ (US); Andrzej J. Chanduszko, Chandler, AZ (US); Michael Randall, Gilbert, AZ (US); Peng Zheng, Chandler, AZ (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 72 days.

(21) Appl. No.: 15/388,335

(22) Filed: Dec. 22, 2016

(65) Prior Publication Data

US 2018/0177515 A1 Jun. 28, 2018

(51) Int. Cl.
*A61B 17/22* (2006.01)
*A61M 25/10* (2013.01)
(Continued)

(52) U.S. Cl.
CPC .......... *A61B 17/2202* (2013.01); *A61B 17/22* (2013.01); *A61B 17/22004* (2013.01);
(Continued)

(58) Field of Classification Search
CPC ...... A61B 17/2202; A61B 2017/22065; A61B 2017/22054; A61B 2017/22062;
(Continued)

(56) References Cited

U.S. PATENT DOCUMENTS

| 3,296,620 A | 1/1967 | Rodda |
| 3,433,226 A | 3/1969 | Boyd |

(Continued)

FOREIGN PATENT DOCUMENTS

| AU | 2007240154 A1 | 1/2008 |
| DE | 2256127 A1 | 5/1974 |

(Continued)

OTHER PUBLICATIONS

Circulation Catheter-Based Ultrasound Thrombolysis Shake, Rattle, and Reperfuse Paul G. Yock, Peter J. Fitzgerald https://doi.org/10.1161/01.CIR.95.6.1360.

(Continued)

*Primary Examiner* — Tan-Uyen T Ho
*Assistant Examiner* — Chima U Igboko

(57) ABSTRACT

A catheter includes a wave guide for transmitting ultrasonic energy from a transducer, and which is also rotated to facilitate enhanced disruption of the concerned obstruction in a transverse direction. Embodiments of waveguide include distal anchors that help focus the energy transmitted to a treatment site, and may also include a deployable filter that may open distal of the obstruction to capture any dislodged debris. Selectively inflatable balloons may cordon off a treatment site, and the wave guide may comprise a tube that may serve the dual purposes of inflating the balloon(s), as well as to transmit ultrasonic energy to an obstruction. A portion of an ultrasonic catheter may include plural curved portions to space an exposed portion of the wave guide away from the catheter body to enhance the vibratory action provided.

8 Claims, 8 Drawing Sheets

(51) Int. Cl.
  *A61M 25/04* (2006.01)
  *A61M 25/00* (2006.01)
(52) U.S. Cl.
  CPC .............. *A61B 2017/22048* (2013.01); *A61B 2017/22051* (2013.01); *A61B 2017/22054* (2013.01); *A61B 2017/22062* (2013.01); *A61B 2017/22065* (2013.01); *A61M 25/0068* (2013.01); *A61M 25/04* (2013.01); *A61M 25/1011* (2013.01); *A61M 2025/1047* (2013.01)
(58) Field of Classification Search
  CPC ........... A61B 2017/22067; A61B 2017/22068; A61B 2017/22069; A61B 2017/22071; A61B 17/320068; A61B 2017/320069; A61B 2017/320082; A61B 2017/320092; A61B 2017/320094; A61B 18/1492; A61M 25/1018; A61M 25/0071; A61M 25/0069; A61M 25/09
  USPC ....... 606/159, 169, 200; 604/101.01, 101.03, 604/101.05
  See application file for complete search history.

(56) References Cited

U.S. PATENT DOCUMENTS

| | | | |
|---|---|---|---|
| 3,443,226 A | 5/1969 | Knight | |
| 3,565,062 A | 2/1971 | Kurls | |
| 3,585,082 A | 6/1971 | Siller | |
| 3,612,038 A | 10/1971 | Halligan | |
| 3,631,848 A | 1/1972 | Muller | |
| 3,679,378 A | 7/1972 | Van Impe et al. | |
| 3,719,737 A | 3/1973 | Vaillancourt et al. | |
| 3,739,460 A | 6/1973 | Addis et al. | |
| 3,754,746 A | 8/1973 | Thiele | |
| 3,823,717 A | 7/1974 | Pohlman et al. | |
| 3,835,690 A | 9/1974 | Leonhardt et al. | |
| 3,839,841 A | 10/1974 | Amplatz | |
| 3,896,811 A | 7/1975 | Storz | |
| 4,016,882 A | 4/1977 | Broadwin et al. | |
| 4,033,331 A | 7/1977 | Guss et al. | |
| 4,136,700 A | 1/1979 | Broadwin et al. | |
| 4,337,090 A | 6/1982 | Harrison | |
| 4,368,410 A | 1/1983 | Hance et al. | |
| 4,417,578 A | 11/1983 | Banko | |
| 4,425,115 A | 1/1984 | Wuchinich | |
| 4,486,680 A | 12/1984 | Bonnet et al. | |
| 4,505,767 A | 3/1985 | Quin | |
| 4,535,759 A | 8/1985 | Polk et al. | |
| 4,545,767 A | 10/1985 | Suzuki et al. | |
| 4,565,589 A | 1/1986 | Harrison | |
| 4,565,787 A | 1/1986 | Bossle et al. | |
| 4,572,184 A | 2/1986 | Stohl et al. | |
| 4,664,112 A | 5/1987 | Kensey et al. | |
| 4,665,906 A | 5/1987 | Jervis | |
| 4,679,558 A | 7/1987 | Kensey et al. | |
| 4,700,705 A | 10/1987 | Kensey et al. | |
| 4,721,117 A | 1/1988 | Mar et al. | |
| 4,750,902 A | 6/1988 | Wuchinich et al. | |
| 4,808,153 A | 2/1989 | Parisi | |
| 4,811,743 A | 3/1989 | Stevens | |
| 4,827,911 A | 5/1989 | Broadwin et al. | |
| 4,838,853 A | 6/1989 | Parisi | |
| 4,854,325 A | 8/1989 | Stevens | |
| 4,870,953 A | 10/1989 | DonMicheal et al. | |
| 4,886,060 A | 12/1989 | Wiksell | |
| 4,920,954 A | 5/1990 | Alliger et al. | |
| 4,923,462 A | 5/1990 | Stevens | |
| 4,924,863 A | 5/1990 | Sterzer | |
| 4,931,047 A | 6/1990 | Broadwin et al. | |
| 4,936,281 A | 6/1990 | Stasz | |
| 4,936,845 A | 6/1990 | Stevens | |
| 5,000,185 A | 3/1991 | Yock | |
| 5,015,227 A | 5/1991 | Broadwin et al. | |
| 5,026,384 A | 6/1991 | Farr et al. | |
| 5,030,357 A | 7/1991 | Lowe | |
| 5,046,503 A | 9/1991 | Schneiderman | |
| 5,053,008 A * | 10/1991 | Bajaj .................... A61F 2/01 604/104 |
| 5,058,570 A | 10/1991 | Idemoto et al. | |
| 5,076,276 A | 12/1991 | Sakurai et al. | |
| 5,091,205 A | 2/1992 | Fan | |
| 5,100,423 A * | 3/1992 | Fearnot .............. A61B 17/2202 606/159 |
| 5,109,859 A | 5/1992 | Jenkins | |
| 5,114,414 A | 5/1992 | Buchbinder | |
| 5,116,350 A | 5/1992 | Stevens | |
| 5,127,917 A | 7/1992 | Niederhauser et al. | |
| 5,156,143 A | 10/1992 | Bocquet et al. | |
| 5,163,421 A | 11/1992 | Bernstein et al. | |
| 5,171,216 A | 12/1992 | Dasse et al. | |
| 5,180,363 A | 1/1993 | Idemoto et al. | |
| 5,183,470 A | 2/1993 | Wettermann | |
| 5,195,955 A | 3/1993 | Don Michael | |
| 5,215,614 A | 6/1993 | Wijkamp et al. | |
| 5,217,565 A | 6/1993 | Kou et al. | |
| 5,221,255 A | 6/1993 | Mahurkar et al. | |
| 5,226,421 A | 7/1993 | Frisbie et al. | |
| 5,234,416 A | 8/1993 | Macaulay et al. | |
| 5,238,004 A | 8/1993 | Sahatjian et al. | |
| 5,242,385 A | 9/1993 | Strukel | |
| 5,243,997 A | 9/1993 | Uflacker et al. | |
| 5,248,296 A | 9/1993 | Alliger | |
| 5,255,669 A | 10/1993 | Kubota et al. | |
| 5,267,954 A | 12/1993 | Nita | |
| 5,269,291 A | 12/1993 | Carter | |
| 5,269,297 A | 12/1993 | Weng et al. | |
| 5,269,793 A | 12/1993 | Simpson | |
| 5,279,546 A * | 1/1994 | Mische .............. A61B 17/22012 604/101.03 |
| 5,287,858 A | 2/1994 | Hammerslag et al. | |
| 5,290,229 A | 3/1994 | Paskar | |
| 5,304,115 A | 4/1994 | Pflueger et al. | |
| 5,304,131 A | 4/1994 | Paskar | |
| 5,312,328 A | 5/1994 | Nita et al. | |
| 5,318,014 A | 6/1994 | Carter | |
| 5,318,570 A | 6/1994 | Hood et al. | |
| 5,324,255 A | 6/1994 | Passafaro et al. | |
| 5,324,260 A | 6/1994 | O'Neill et al. | |
| 5,325,860 A | 7/1994 | Seward et al. | |
| 5,326,342 A | 7/1994 | Pflueger et al. | |
| 5,328,004 A | 7/1994 | Fannin et al. | |
| 5,329,927 A | 7/1994 | Gardineer et al. | |
| 5,341,818 A | 8/1994 | Abrams et al. | |
| 5,342,292 A | 8/1994 | Nita et al. | |
| 5,344,395 A | 9/1994 | Whalen et al. | |
| 5,346,502 A | 9/1994 | Estabrook et al. | |
| 5,362,309 A | 11/1994 | Carter | |
| 5,368,557 A | 11/1994 | Nita | |
| 5,368,558 A | 11/1994 | Nita et al. | |
| 5,376,084 A | 12/1994 | Bacich et al. | |
| 5,378,234 A | 1/1995 | Hammerslag et al. | |
| 5,380,274 A | 1/1995 | Nita | |
| 5,380,316 A | 1/1995 | Aita et al. | |
| 5,382,228 A | 1/1995 | Nita et al. | |
| 5,383,460 A | 1/1995 | Jang et al. | |
| 5,389,096 A | 2/1995 | Aita et al. | |
| 5,391,144 A | 2/1995 | Sakurai et al. | |
| 5,397,293 A | 3/1995 | Alliger et al. | |
| 5,397,301 A | 3/1995 | Pflueger et al. | |
| 5,405,318 A | 4/1995 | Nita | |
| 5,409,483 A | 4/1995 | Campbell et al. | |
| 5,417,672 A | 5/1995 | Nita et al. | |
| 5,417,703 A | 5/1995 | Brown et al. | |
| 5,421,923 A | 6/1995 | Clarke et al. | |
| 5,427,118 A | 6/1995 | Nita et al. | |
| 5,431,168 A | 7/1995 | Webster, Jr. | |
| 5,431,663 A | 7/1995 | Carter | |
| 5,443,078 A | 8/1995 | Uflacker | |
| 5,447,509 A | 9/1995 | Mills et al. | |
| 5,449,369 A | 9/1995 | Imran | |
| 5,451,209 A | 9/1995 | Ainsworth et al. | |

(56) References Cited

U.S. PATENT DOCUMENTS

| | | | |
|---|---|---|---|
| 5,462,529 A * | 10/1995 | Simpson | A61B 17/320758 604/101.04 |
| 5,465,733 A | 11/1995 | Hinohara et al. | |
| 5,474,530 A | 12/1995 | Passafaro et al. | |
| 5,474,531 A | 12/1995 | Carter | |
| 5,480,379 A | 1/1996 | La Rosa | |
| 5,484,398 A | 1/1996 | Stoddard | |
| 5,487,757 A | 1/1996 | Truckai et al. | |
| 5,498,236 A | 3/1996 | Dubrul et al. | |
| 5,507,738 A | 4/1996 | Ciervo | |
| 5,516,043 A | 5/1996 | Manna et al. | |
| 5,527,273 A | 6/1996 | Manna et al. | |
| 5,540,656 A | 7/1996 | Pflueger et al. | |
| 5,542,917 A | 8/1996 | Nita et al. | |
| 5,597,497 A | 1/1997 | Dean et al. | |
| 5,597,882 A | 1/1997 | Schiller et al. | |
| 5,607,421 A | 3/1997 | Jeevanandam et al. | |
| 5,611,807 A | 3/1997 | O'Boyle | |
| 5,618,266 A | 4/1997 | Liprie | |
| 5,626,593 A | 5/1997 | Imran | |
| 5,627,365 A | 5/1997 | Chiba et al. | |
| 5,649,935 A | 7/1997 | Kremer et al. | |
| 5,658,282 A | 8/1997 | Daw et al. | |
| 5,685,841 A | 11/1997 | Mackool | |
| 5,695,460 A | 12/1997 | Siegel et al. | |
| 5,695,507 A | 12/1997 | Auth et al. | |
| 5,715,825 A | 2/1998 | Crowley | |
| 5,720,724 A | 2/1998 | Ressemann et al. | |
| 5,728,062 A | 3/1998 | Brisken | |
| 5,738,100 A | 4/1998 | Yagami et al. | |
| 5,797,876 A | 8/1998 | Spears et al. | |
| 5,816,923 A | 10/1998 | Milo et al. | |
| 5,827,203 A | 10/1998 | Nita | |
| 5,827,971 A | 10/1998 | Hale et al. | |
| 5,830,222 A | 11/1998 | Makower | |
| 5,846,218 A | 12/1998 | Brisken et al. | |
| 5,893,838 A | 4/1999 | Daoud et al. | |
| 5,895,397 A | 4/1999 | Jang et al. | |
| 5,902,287 A | 5/1999 | Martin | |
| 5,904,667 A | 5/1999 | Falwell | |
| 5,913,192 A | 6/1999 | Parthasarathy et al. | |
| 5,916,192 A | 6/1999 | Nita et al. | |
| 5,916,912 A | 6/1999 | Ames et al. | |
| 5,935,142 A | 8/1999 | Hood | |
| 5,935,144 A | 8/1999 | Estabrook | |
| 5,937,301 A | 8/1999 | Gardner et al. | |
| 5,944,737 A | 8/1999 | Tsonton et al. | |
| 5,957,882 A | 9/1999 | Nita et al. | |
| 5,957,899 A | 9/1999 | Spears et al. | |
| 5,964,223 A | 10/1999 | Baran | |
| 5,967,984 A | 10/1999 | Chu et al. | |
| 5,971,949 A | 10/1999 | Levin et al. | |
| 5,976,119 A | 11/1999 | Spears et al. | |
| 5,989,208 A | 11/1999 | Nita | |
| 5,989,275 A | 11/1999 | Estabrook et al. | |
| 5,997,497 A | 12/1999 | Nita et al. | |
| 6,004,280 A | 12/1999 | Buck et al. | |
| 6,007,499 A | 12/1999 | Martin et al. | |
| 6,007,514 A | 12/1999 | Nita | |
| 6,022,309 A | 2/2000 | Celliers et al. | |
| 6,024,764 A | 2/2000 | Schroeppel | |
| 6,029,671 A | 2/2000 | Stevens et al. | |
| 6,030,357 A | 2/2000 | Daoud et al. | |
| 6,051,010 A | 4/2000 | DiMatteo et al. | |
| 6,113,558 A | 9/2000 | Rosenschein et al. | |
| 6,123,698 A | 9/2000 | Spears et al. | |
| 6,142,971 A | 11/2000 | Daoud et al. | |
| 6,149,596 A | 11/2000 | Bancroft | |
| 6,159,176 A | 12/2000 | Broadwin et al. | |
| 6,165,127 A | 12/2000 | Crowley | |
| 6,165,188 A | 12/2000 | Saadat et al. | |
| 6,179,809 B1 | 1/2001 | Khairkhahan et al. | |
| 6,180,059 B1 | 1/2001 | Divino, Jr. et al. | |
| 6,190,353 B1 | 2/2001 | Makower et al. | |
| 6,206,842 B1 | 3/2001 | Tu et al. | |
| 6,210,356 B1 | 4/2001 | Anderson et al. | |
| 6,217,543 B1 | 4/2001 | Anis et al. | |
| 6,217,565 B1 | 4/2001 | Cohen | |
| 6,217,588 B1 | 4/2001 | Jerger et al. | |
| 6,221,015 B1 | 4/2001 | Yock | |
| 6,231,546 B1 | 5/2001 | Milo et al. | |
| 6,231,587 B1 | 5/2001 | Makower | |
| 6,235,007 B1 | 5/2001 | Divino, Jr. et al. | |
| 6,241,692 B1 | 6/2001 | Tu et al. | |
| 6,241,703 B1 | 6/2001 | Levin et al. | |
| 6,248,087 B1 | 6/2001 | Spears et al. | |
| 6,277,084 B1 | 8/2001 | Abele et al. | |
| 6,283,983 B1 | 9/2001 | Makower et al. | |
| 6,287,271 B1 | 9/2001 | Dubrul et al. | |
| 6,287,285 B1 | 9/2001 | Michal et al. | |
| 6,287,317 B1 | 9/2001 | Makower et al. | |
| 6,296,620 B1 | 10/2001 | Gesswein et al. | |
| 6,298,620 B1 | 10/2001 | Hatzinikolas | |
| 6,302,875 B1 | 10/2001 | Makower et al. | |
| 6,309,358 B1 | 10/2001 | Okubo | |
| 6,315,741 B1 | 11/2001 | Martin et al. | |
| 6,315,754 B1 | 11/2001 | Daoud et al. | |
| 6,331,171 B1 | 12/2001 | Cohen | |
| 6,346,192 B2 | 2/2002 | Buhr et al. | |
| 6,379,378 B1 | 4/2002 | Werneth et al. | |
| 6,387,109 B1 | 5/2002 | Davison et al. | |
| 6,387,324 B1 | 5/2002 | Patterson et al. | |
| 6,394,956 B1 | 5/2002 | Chandrasekaran et al. | |
| 6,398,736 B1 | 6/2002 | Seward | |
| 6,409,673 B2 | 6/2002 | Yock | |
| 6,416,533 B1 | 7/2002 | Gobin et al. | |
| 6,423,026 B1 | 7/2002 | Gesswein et al. | |
| 6,427,118 B1 | 7/2002 | Suzuki | |
| 6,433,464 B2 | 8/2002 | Jones | |
| 6,434,418 B1 | 8/2002 | Neal et al. | |
| 6,450,975 B1 | 9/2002 | Brennan et al. | |
| 6,454,757 B1 | 9/2002 | Nita et al. | |
| 6,454,997 B1 | 9/2002 | Divino, Jr. et al. | |
| 6,484,052 B1 | 11/2002 | Visuri et al. | |
| 6,491,707 B2 | 12/2002 | Makower et al. | |
| 6,494,891 B1 | 12/2002 | Cornish et al. | |
| 6,494,894 B2 | 12/2002 | Mirarchi | |
| 6,500,141 B1 | 12/2002 | Irion et al. | |
| 6,508,781 B1 | 1/2003 | Brennan et al. | |
| 6,508,784 B1 | 1/2003 | Shu | |
| 6,511,458 B2 | 1/2003 | Milo et al. | |
| 6,524,251 B2 | 2/2003 | Rabiner et al. | |
| 6,533,766 B1 | 3/2003 | Patterson et al. | |
| 6,544,215 B1 | 4/2003 | Bencini et al. | |
| 6,547,754 B1 | 4/2003 | Evans et al. | |
| 6,551,337 B1 | 4/2003 | Rabiner et al. | |
| 6,554,846 B2 | 4/2003 | Hamilton et al. | |
| 6,555,059 B1 | 4/2003 | Myrick et al. | |
| 6,558,502 B2 | 5/2003 | Divino, Jr. et al. | |
| 6,562,031 B2 | 5/2003 | Chandrasekaran et al. | |
| 6,573,470 B1 | 6/2003 | Brown et al. | |
| 6,576,807 B1 | 6/2003 | Brunelot et al. | |
| 6,582,387 B2 | 6/2003 | Derek et al. | |
| 6,589,253 B1 | 7/2003 | Cornish et al. | |
| 6,595,989 B1 | 7/2003 | Schaer | |
| 6,596,235 B2 | 7/2003 | Divino, Jr. et al. | |
| 6,602,467 B1 | 8/2003 | Divino, Jr. et al. | |
| 6,602,468 B2 | 8/2003 | Patterson et al. | |
| 6,605,217 B2 | 8/2003 | Buhr et al. | |
| 6,607,698 B1 | 8/2003 | Spears et al. | |
| 6,610,077 B1 | 8/2003 | Hancock et al. | |
| 6,613,280 B2 | 9/2003 | Myrick et al. | |
| 6,615,062 B2 | 9/2003 | Ryan et al. | |
| 6,616,617 B1 | 9/2003 | Ferrera et al. | |
| 6,622,542 B2 | 9/2003 | Derek et al. | |
| 6,623,448 B2 | 9/2003 | Slater | |
| 6,635,017 B1 | 10/2003 | Moehring et al. | |
| 6,650,923 B1 | 11/2003 | Lesh et al. | |
| 6,652,547 B2 | 11/2003 | Rabiner et al. | |
| 6,660,013 B2 | 12/2003 | Rabiner et al. | |
| 6,676,900 B1 | 1/2004 | Divino, Jr. et al. | |
| 6,682,502 B2 | 1/2004 | Bond et al. | |
| 6,685,657 B2 | 2/2004 | Jones | |
| 6,689,086 B1 | 2/2004 | Nita et al. | |

(56) References Cited

U.S. PATENT DOCUMENTS

| | | | |
|---|---|---|---|
| 6,695,781 B2 | 2/2004 | Rabiner et al. |
| 6,695,782 B2 | 2/2004 | Ranucci et al. |
| 6,695,810 B2 | 2/2004 | Peacock, III et al. |
| 6,702,748 B1 | 3/2004 | Nita et al. |
| 6,702,750 B2 | 3/2004 | Yock |
| 6,719,715 B2 | 4/2004 | Newman et al. |
| 6,719,725 B2 | 4/2004 | Milo et al. |
| 6,729,334 B1 | 5/2004 | Baran |
| 6,733,451 B2 | 5/2004 | Rabiner et al. |
| 6,758,846 B2 | 7/2004 | Goble et al. |
| 6,761,698 B2 | 7/2004 | Shibata et al. |
| 6,855,123 B2 | 2/2005 | Nita |
| 6,866,670 B2 | 3/2005 | Rabiner et al. |
| 6,936,025 B1 | 8/2005 | Evans et al. |
| 6,936,056 B2 | 8/2005 | Nash et al. |
| 6,942,620 B2 | 9/2005 | Nita et al. |
| 6,942,677 B2 | 9/2005 | Nita et al. |
| 6,955,680 B2 | 10/2005 | Satou et al. |
| 7,004,173 B2 | 2/2006 | Sparks et al. |
| 7,004,176 B2 | 2/2006 | Lau |
| 7,056,294 B2 | 6/2006 | Khairkhahan et al. |
| 7,131,983 B2 | 11/2006 | Murakami |
| 7,137,963 B2 | 11/2006 | Nita et al. |
| 7,149,587 B2 | 12/2006 | Wardle et al. |
| 7,150,853 B2 | 12/2006 | Lee et al. |
| 7,166,098 B1 | 1/2007 | Steward et al. |
| 7,220,233 B2 | 5/2007 | Nita et al. |
| 7,267,650 B2 | 9/2007 | Chow et al. |
| 7,297,131 B2 | 11/2007 | Nita |
| 7,335,180 B2 | 2/2008 | Nita et al. |
| 7,341,569 B2 | 3/2008 | Soltani et al. |
| 7,384,407 B2 | 6/2008 | Rodriguez et al. |
| 7,393,338 B2 | 7/2008 | Nita |
| 7,421,900 B2 | 9/2008 | Karasawa et al. |
| 7,425,198 B2 | 9/2008 | Moehring et al. |
| 7,494,468 B2 | 2/2009 | Rabiner et al. |
| 7,503,895 B2 | 3/2009 | Rabiner et al. |
| 7,540,852 B2* | 6/2009 | Nita ................. A61B 17/22004 |
| | | | 604/22 |
| 7,604,608 B2 | 10/2009 | Nita et al. |
| 7,621,902 B2 | 11/2009 | Nita et al. |
| 7,621,929 B2 | 11/2009 | Nita et al. |
| 7,648,478 B2 | 1/2010 | Soltani et al. |
| 7,771,358 B2 | 8/2010 | Moehring et al. |
| 7,771,452 B2 | 8/2010 | Pal et al. |
| 7,775,994 B2 | 8/2010 | Lockhart |
| 7,776,025 B2 | 8/2010 | Bobo, Jr. |
| 7,819,013 B2 | 10/2010 | Chan et al. |
| 7,850,623 B2 | 12/2010 | Griffin et al. |
| 7,918,819 B2 | 4/2011 | Karmarkar et al. |
| 7,935,108 B2 | 5/2011 | Baxter et al. |
| 7,938,819 B2 | 5/2011 | Kugler et al. |
| 7,955,293 B2 | 6/2011 | Nita et al. |
| 8,043,251 B2 | 10/2011 | Nita et al. |
| 8,083,727 B2 | 12/2011 | Kugler et al. |
| 8,133,236 B2 | 3/2012 | Nita |
| 8,221,343 B2 | 7/2012 | Nita et al. |
| 8,226,566 B2 | 7/2012 | Nita |
| 8,246,643 B2 | 8/2012 | Nita |
| 8,257,378 B1 | 9/2012 | O'Connor |
| 8,308,677 B2 | 11/2012 | Nita et al. |
| 8,414,543 B2 | 4/2013 | McGuckin, Jr. et al. |
| 8,506,519 B2 | 8/2013 | Nita |
| 8,613,751 B2 | 12/2013 | Nita et al. |
| 8,617,096 B2 | 12/2013 | Nita et al. |
| 8,632,560 B2 | 1/2014 | Pal et al. |
| 8,647,296 B2 | 2/2014 | Moberg et al. |
| 8,663,259 B2 | 3/2014 | Levine et al. |
| 8,668,709 B2 | 3/2014 | Nita et al. |
| 8,690,818 B2 | 4/2014 | Bennett et al. |
| 8,690,819 B2 | 4/2014 | Nita et al. |
| 8,764,700 B2 | 7/2014 | Zhang et al. |
| 8,790,291 B2 | 7/2014 | Nita et al. |
| 8,974,446 B2 | 3/2015 | Nguyen et al. |
| 9,107,590 B2 | 8/2015 | Hansmann et al. |
| 9,265,520 B2 | 2/2016 | Nita |
| 9,282,984 B2 | 3/2016 | Nita |
| 9,314,258 B2 | 4/2016 | Nita et al. |
| 9,381,027 B2 | 7/2016 | Nita et al. |
| 9,421,024 B2 | 8/2016 | Nita et al. |
| 9,770,250 B2 | 9/2017 | Nita et al. |
| 10,004,520 B2 | 6/2018 | Nita et al. |
| 2002/0022858 A1* | 2/2002 | Demond ................. A61F 2/01 |
| | | | 606/200 |
| 2002/0029054 A1 | 3/2002 | Rabiner et al. |
| 2002/0049409 A1 | 4/2002 | Noda et al. |
| 2002/0077550 A1 | 6/2002 | Rabiner et al. |
| 2002/0188276 A1* | 12/2002 | Evans ................. A61B 17/22 |
| | | | 604/509 |
| 2003/0009153 A1 | 1/2003 | Brisken et al. |
| 2003/0036705 A1 | 2/2003 | Hare et al. |
| 2003/0040762 A1 | 2/2003 | Dorros et al. |
| 2003/0176791 A1 | 9/2003 | Rabiner et al. |
| 2003/0199817 A1 | 10/2003 | Thompson et al. |
| 2003/0216732 A1 | 11/2003 | Truckai et al. |
| 2003/0225332 A1 | 12/2003 | Okada et al. |
| 2004/0024393 A1 | 2/2004 | Nita et al. |
| 2004/0164030 A1 | 8/2004 | Lowe et al. |
| 2004/0167511 A1* | 8/2004 | Buehlmann ........ A61B 18/1492 |
| | | | 606/45 |
| 2005/0033311 A1 | 2/2005 | Guldfeldt et al. |
| 2005/0113688 A1 | 5/2005 | Nita et al. |
| 2005/0149110 A1* | 7/2005 | Wholey ................. A61F 2/013 |
| | | | 606/200 |
| 2005/0228286 A1 | 10/2005 | Messerly et al. |
| 2006/0074441 A1* | 4/2006 | McGuckin, Jr. ...... A61B 17/22 |
| | | | 606/159 |
| 2006/0206039 A1 | 9/2006 | Wilson et al. |
| 2006/0264809 A1 | 11/2006 | Hansmann et al. |
| 2007/0037119 A1* | 2/2007 | Pal .................... A61B 17/22012 |
| | | | 433/119 |
| 2008/0071343 A1 | 3/2008 | Mayberry et al. |
| 2008/0208084 A1 | 8/2008 | Horzewski et al. |
| 2008/0221506 A1 | 9/2008 | Rodriguez et al. |
| 2009/0264770 A1* | 10/2009 | Liu .................. A61B 17/22012 |
| | | | 600/466 |
| 2010/0023037 A1 | 1/2010 | Nita et al. |
| 2011/0105960 A1 | 5/2011 | Wallace |
| 2011/0130834 A1 | 6/2011 | Wilson et al. |
| 2011/0237982 A1 | 9/2011 | Wallace |
| 2011/0313328 A1 | 12/2011 | Nita |
| 2012/0130475 A1 | 5/2012 | Shaw |
| 2012/0311844 A1 | 12/2012 | Nita et al. |
| 2012/0330196 A1 | 12/2012 | Nita |
| 2014/0236118 A1 | 8/2014 | Unser et al. |
| 2014/0243712 A1 | 8/2014 | Humayun et al. |
| 2015/0133918 A1 | 5/2015 | Sachar |
| 2015/0150571 A1 | 6/2015 | Nita et al. |
| 2015/0157443 A1 | 6/2015 | Hauser et al. |
| 2015/0190660 A1 | 7/2015 | Sarge et al. |
| 2015/0297258 A1 | 10/2015 | Escudero et al. |
| 2015/0359651 A1 | 12/2015 | Wübbeling |
| 2016/0128717 A1 | 5/2016 | Nita |
| 2016/0183956 A1 | 6/2016 | Nita |
| 2016/0271362 A1 | 9/2016 | Van Liere |
| 2016/0338722 A1 | 11/2016 | Nita et al. |
| 2017/0065288 A1* | 3/2017 | Imai ............... A61B 17/320725 |
| 2017/0354428 A1 | 12/2017 | Nita et al. |

FOREIGN PATENT DOCUMENTS

| | | |
|---|---|---|
| DE | 2438648 A1 | 2/1976 |
| DE | 8910040 U1 | 12/1989 |
| DE | 3821836 A1 | 1/1990 |
| DE | 4042435 C2 | 2/1994 |
| EP | 0005719 A1 | 12/1979 |
| EP | 0316789 A2 | 5/1989 |
| EP | 0316796 A2 | 5/1989 |
| EP | 0376562 A2 | 7/1990 |
| EP | 0379156 A2 | 7/1990 |
| EP | 0394583 A2 | 10/1990 |
| EP | 0443256 A1 | 8/1991 |
| EP | 0472368 A2 | 2/1992 |

(56) References Cited

FOREIGN PATENT DOCUMENTS

| | | |
|---|---|---|
| EP | 0541249 A2 | 5/1993 |
| EP | 0820728 A2 | 1/1998 |
| EP | 1323481 A2 | 7/2003 |
| GB | 1106957 | 3/1968 |
| JP | H2-7150 U | 10/1988 |
| JP | 01-099547 | 4/1989 |
| JP | 6086822 A | 3/1994 |
| JP | H07500752 A | 1/1995 |
| JP | 7116260 A | 5/1995 |
| JP | 9-503137 | 3/1997 |
| JP | 10-216140 | 8/1998 |
| JP | 2000-291543 | 10/2000 |
| JP | 2001-104356 | 4/2001 |
| JP | 2001-321388 | 11/2001 |
| JP | 2002-186627 | 7/2002 |
| JP | 2005-253874 | 9/2005 |
| JP | 2006-522644 A | 10/2006 |
| JP | 2007512087 A | 5/2007 |
| JP | 2007520255 A | 7/2007 |
| WO | 8705739 A1 | 9/1987 |
| WO | 8705793 A1 | 10/1987 |
| WO | 8906515 A1 | 7/1989 |
| WO | 9001300 A1 | 2/1990 |
| WO | 9004362 A1 | 5/1990 |
| WO | 9107917 A2 | 6/1991 |
| WO | 9211815 A2 | 7/1992 |
| WO | 9308750 A2 | 5/1993 |
| WO | 9316646 A1 | 9/1993 |
| WO | 9412140 A1 | 6/1994 |
| WO | 9414382 A1 | 7/1994 |
| WO | 9508954 A1 | 4/1995 |
| WO | 9509571 A1 | 4/1995 |
| WO | 9515192 A1 | 6/1995 |
| WO | 9635469 A1 | 11/1996 |
| WO | 9705739 A1 | 2/1997 |
| WO | 9721462 A1 | 6/1997 |
| WO | 9745078 A1 | 12/1997 |
| WO | 9827874 A1 | 7/1998 |
| WO | 9835721 A2 | 8/1998 |
| WO | 9851224 A2 | 11/1998 |
| WO | 9852637 A1 | 11/1998 |
| WO | 9925412 A2 | 5/1999 |
| WO | 0053341 A1 | 9/2000 |
| WO | 0067830 A1 | 11/2000 |
| WO | 03039381 A1 | 5/2003 |
| WO | 2004012609 A1 | 2/2004 |
| WO | 2004093736 A2 | 11/2004 |
| WO | 2004112888 A2 | 12/2004 |
| WO | 2005053769 A2 | 6/2005 |
| WO | 2006049593 A1 | 5/2006 |
| WO | 2014022716 A2 | 2/2014 |
| WO | 2014105754 A1 | 7/2014 |
| WO | WO2014105754 A1 | 7/2014 |
| WO | WO2016064077 | 4/2016 |

OTHER PUBLICATIONS

Japanese Office Action for Japanese Application No. 2010-134566, dated Mar. 2, 2012.
Sehgal, et al., Ultrasound-Assisted Thrombolysis, Investigative Radiology, 1993, vol. 28, Issue 10, pp. 939-943.
Siegel, et al., "In Vivo Ultrasound Arterial Recanalization of Atherosclerotic Total Occlusions", Journal of the American College of Cardiology, Feb. 1990, vol. 15, No. 2, pp. 345-351.
"What is Electron Beam Curing?" downloaded from web on Nov. 14, 2002, 4 pages total. <http://www.ms.oml.gov/researchgroups/composites/new%20orccmt%20pages/pages/ebwha>.
Noone, D.: Experimental and Numerical Investigation of Wire Waveguides for Therapeutic Ultrasound Angioplasty. M.Eng. Dublin City University. 2008.
Definition of the term "connected", retrieved on Sep. 21, 2013. <www.thefreedictionary.com/connected> 1 page total.
Supplemental European Search Report dated Nov. 5, 2009 for European Application No. EP03766931.
International Search Report dated Oct. 28, 2003 for PCT Application No. PCT/US2003/023468.
Extended European Search Report dated Mar. 22, 2012 for European Application No. EP11188799.
International Search Report dated Dec. 23, 2005 for PCT Application No. PCT/US2004/019378.
Extended European Search Report for Patent Application No. 06718204.8, dated May 30, 2012.
International Search Report dated Aug. 1, 2013 for PCT Application No. PCT/US2013/053306.
International Preliminary Report dated Aug. 1, 2013 for PCT Application No. PCT/US2013/053306.
Written Opinion dated Aug. 1, 2013 for PCT Application No. PCT/US2013/053306.
Supplemental European Search Report dated Apr. 29, 2009 for European Application No. EP 04711207.3.
Calhoun et al., "Electron-Beam Systems for Medical Device Sterilization", downloaded from web on Oct. 8, 2002 <http://www.devicelink.com/mpb/archive/97/07/002.html> 7 pages total.
Definition of the term "coupled", retrieved on May 18, 2013. <http://www.merriam-webster.com/dictionary/couple> 1 page total.
"E-Beam Theory" RDI-IBA Technology Group, downloaded from web on Oct. 8, 2002 <http://www.e-beamrdi/EbeamTheory.htm> 2 pages total.
Office Action dated May 20, 2010 from Japanese Application No. 2006-541200 filed on Oct. 25, 2004.
Office Action dated Oct. 11, 2012 from Japanese Application No. 2010-181956.
Extended European Search Report dated Mar. 5, 2012 for European Application No. 12153606.4-1269.
Margaret Fyfe et al., Mast cell degranulation and increased vascular permeability induced by 'therapeutic' ultrasound in the rate ankle joint, Br. J. exp. Path., 1984, vol. 65, pp. 671-676.
"Irradiation, Biological, and Other Technologies: E-beam, Biological, and Sharps Treatment Systems", Non-Incineration Medical Waste Treatment Technologies, Aug. 2001, Chapter 9, pp. 69-74, Health Care Without Harm, Washington, DC.

\* cited by examiner

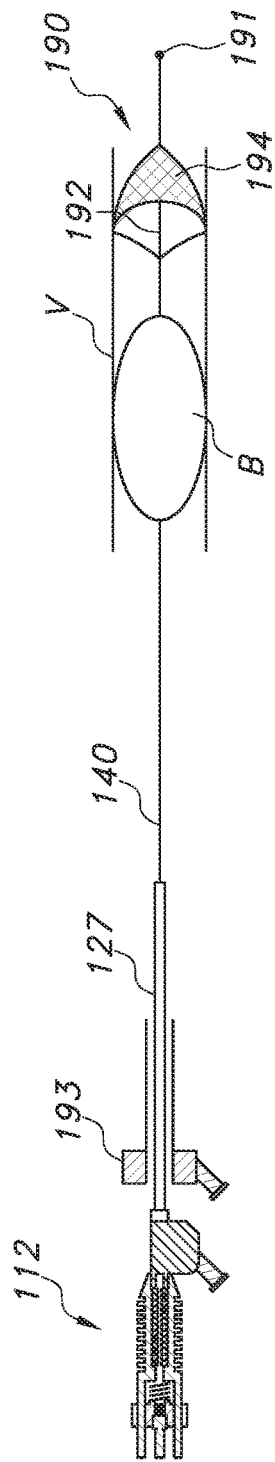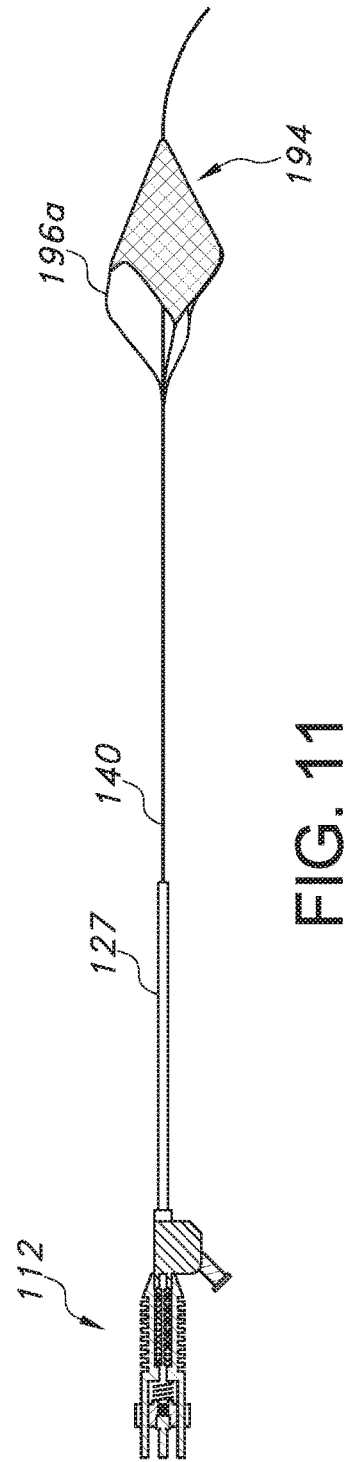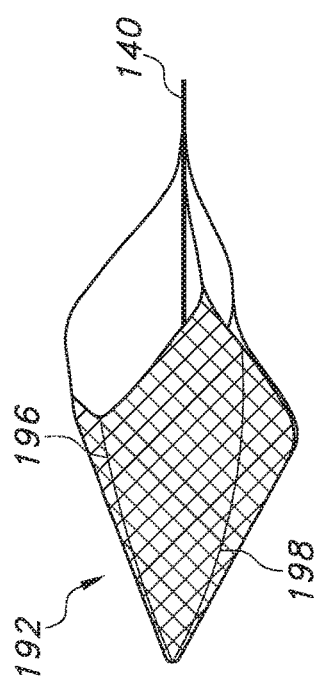
FIG. 10
FIG. 11
FIG. 12

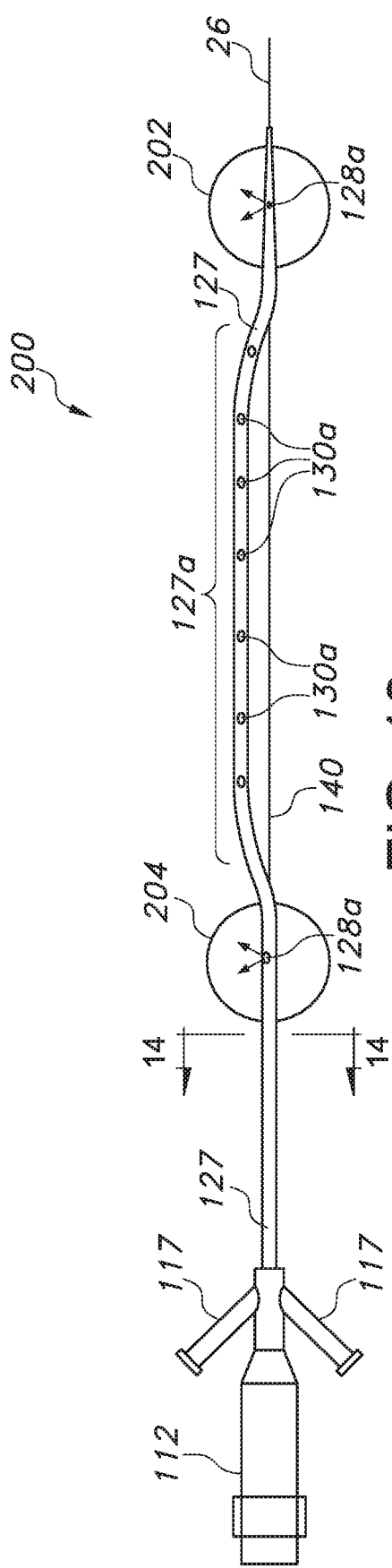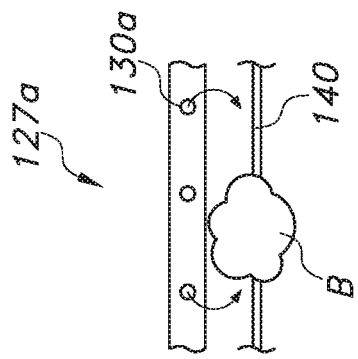

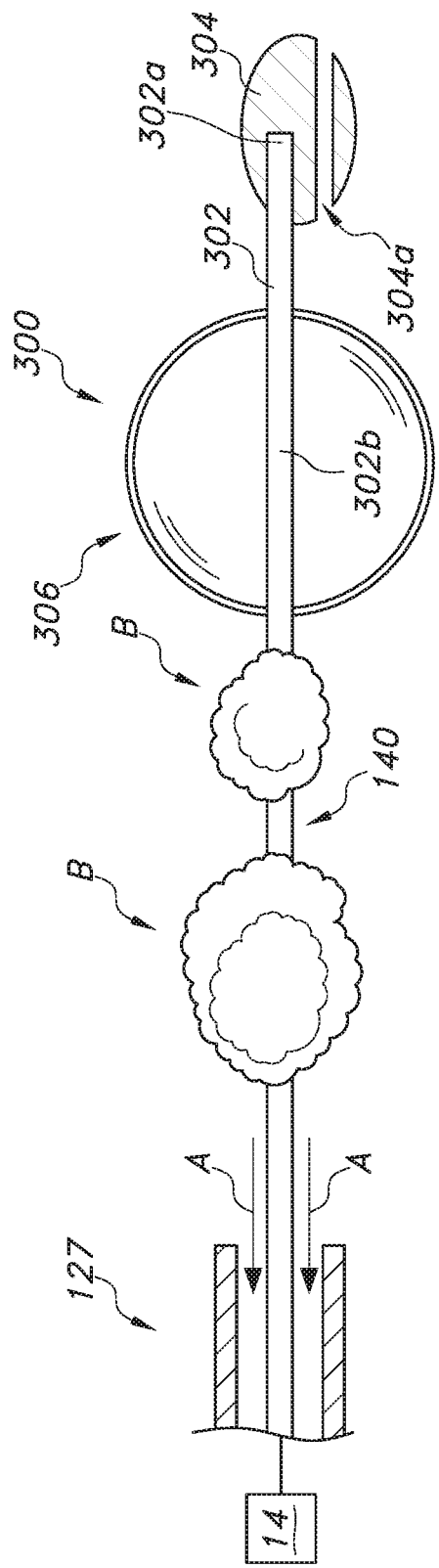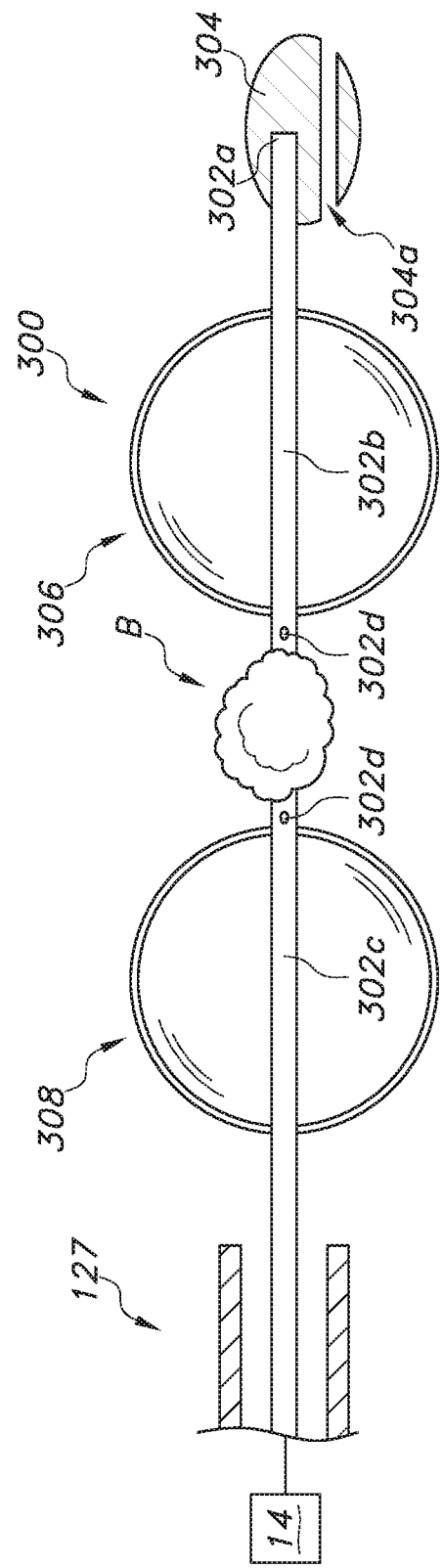

ULTRASONIC ENDOVASCULAR CATHETER

TECHNICAL FIELD

This document relates generally to the art of endovascular procedures and, more particularly, to an endovascular catheter using ultrasonic energy to perform a medical procedure, such as an atherectomy or thrombectomy.

BACKGROUND

Ultrasonic catheters have been proposed. An example of such a catheter is shown in U.S. Pat. No. 7,540,852, the disclosure of which is fully incorporated herein by reference. While this catheter achieves the desired result of providing enhanced disruption of blood vessel obstructions, the present disclosure proposes certain modifications or improvements to enhance the results achieved during an endovascular procedure in terms of clearing an obstruction from a vessel (such as, for example, an atherectomy for removing atherosclerosis from a blood vessel or or a thrombectomy for dissolving a thrombus or embolus).

SUMMARY

Summarizing the disclosure, an improved ultrasonic catheter for enhancing an endovascular procedure, such as an atherectomy or thrombectomy. The catheter may include a wave guide for transmitting ultrasonic energy from a transducer, and which is also rotated by a motor to facilitate enhanced disruption of the concerned obstruction in a transverse direction. Embodiments of waveguide include distal anchors that help prevent movement of the distal end, and may also include a deployable filter that may open distal of the obstruction to capture any dislodged debris (which may be suctioned out through a lumen in an associated catheter body).

To help improve the treatment regimen, an ultrasonic catheter may also be provided with barriers, such as inflatable balloons, to cordon off a treatment site. In any embodiment including one or more balloons, the waveguide may serve the dual purposes of inflating the balloon(s), as well as transmitting ultrasonic energy to an obstruction. To further enhance the energy transmission for treatment purposes, a portion of the ultrasonic catheter may include one or more curves (possibly selectively actuated by way of a remote control) in order to space an exposed portion of the wave guide away from the catheter body to thereby enhance the vibratory action provided.

According to a first specific aspect of the disclosure, an apparatus for performing an endovascular procedure is provided. The apparatus comprises a catheter and an associated wave guide having a distal end portion adapted for extending from the lumen of the catheter. An actuator for vibrating and rotating the wave guide is also provided.

In one embodiment, the actuator comprises an ultrasonic transducer for vibrating the wave guide and a motor for rotating the ultrasonic transducer or the wave guide. The catheter may include a lumen for receiving a proximal portion of the wave guide, which may include a distal portion having at least one curve or bend. A connector connected to the catheter may at least partially include the actuator, and a controller may be provided for controlling the amount and direction of rotation of the wave guide.

According to a further aspect of the disclosure, an apparatus for performing an endovascular procedure comprises a catheter and a wave guide associated with the catheter. The wave guide includes a distal end with an anchor for anchoring the wave guide. An actuator is also provided for vibrating the wave guide.

In one embodiment, the anchor comprises a centering coil. In another embodiment, the anchor comprises one or more weights. In still another embodiment, the anchor comprises an anchoring cone, and in another is an inflatable balloon. The wave guide may comprise a wire.

Still a further aspect of the disclosure pertains to an apparatus for performing an endovascular procedure. The apparatus comprises a catheter and a wave guide associated with the catheter. The wave guide includes a distal end having a filter with an open end facing a proximal end of the wave guide. An actuator is also provided for vibrating the wave guide.

In one embodiment, the filter comprises a deployable frame supporting a flexible material. The deployable frame may comprise a shape memory material. The flexible material may comprise a porous mesh or similar material for performing a filtering function.

Yet a further aspect of the disclosure pertains to an apparatus for performing an endovascular procedure. The apparatus comprises a catheter including a lumen and supporting a first inflatable balloon. A wave guide includes a distal end portion projecting from the lumen proximally of the first inflatable balloon. An actuator is provided for actuating the wave guide.

In one embodiment, the wave guide comprises a tube for supplying inflation fluid to the first balloon. The apparatus may further include a second balloon, and the wave guide may comprise a wire extending between the first and second balloons. A portion of the catheter between the first and second balloons may comprise one or more openings for transmitting fluid to or from a portion of a vessel bounded by the first and second balloons when inflated.

Another aspect of the disclosure pertains to an apparatus for performing an endovascular procedure. The apparatus comprises a catheter including a lumen extending along a proximal end portion and a distal end portion. A wave guide includes a first portion positioned within the lumen, a second exposed portion, and a third portion connected to the distal end portion of the catheter. An actuator is provided for vibrating at least the second exposed portion of the wave guide.

In a further aspect, the disclosure pertains to an apparatus for performing an endovascular procedure. The apparatus comprises a catheter including a proximal end portion including a lumen and opposed portions. A wave guide includes a first portion positioned within the lumen and a second exposed portion positioned along the opposed portions of the catheter.

In one embodiment, an actuator is provided for vibrating the wave guide. The catheter may also include opposed curved portions. The wave guide may be positioned in a gap or space between the opposed curved portions, which may surround the wave guide (e.g., core wire or tube).

Yet another aspect of the disclosure pertains to an apparatus for performing an endovascular procedure. A catheter supports a first inflatable balloon. A wave guide is associated with the catheter and includes a lumen. An actuator, such as an ultrasonic transducer, is provided for coupling to a proximal end of the wave guide.

In one embodiment, the apparatus further includes a second inflatable balloon supported by the tube proximally of the first inflatable balloon. A tip may also be provided for sealing a distal end of the tube. The tip may include a guidewire lumen.

BRIEF DESCRIPTION OF THE DRAWING FIGURES

The accompanying drawing figures incorporated herein and forming a part of the specification, illustrate several aspects of the ultrasonic endovascular catheter and, together with the description, serve to explain certain principles thereof. In the drawing figures.

Figure 7:
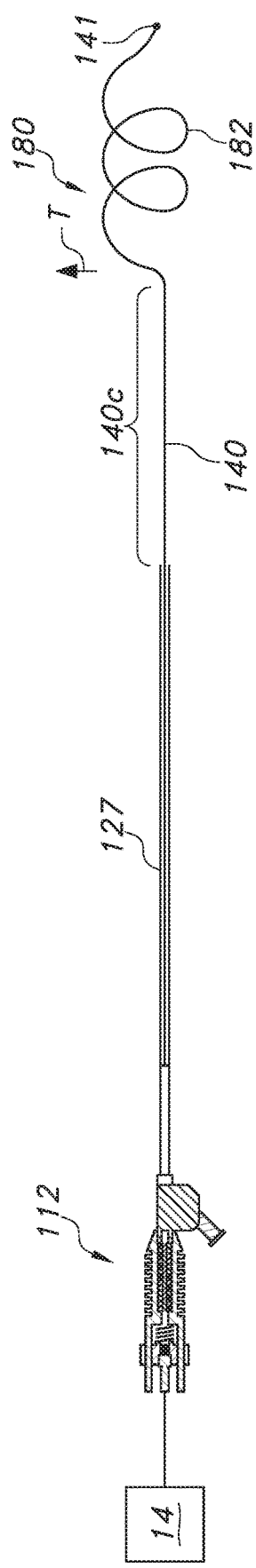
Figure 8:
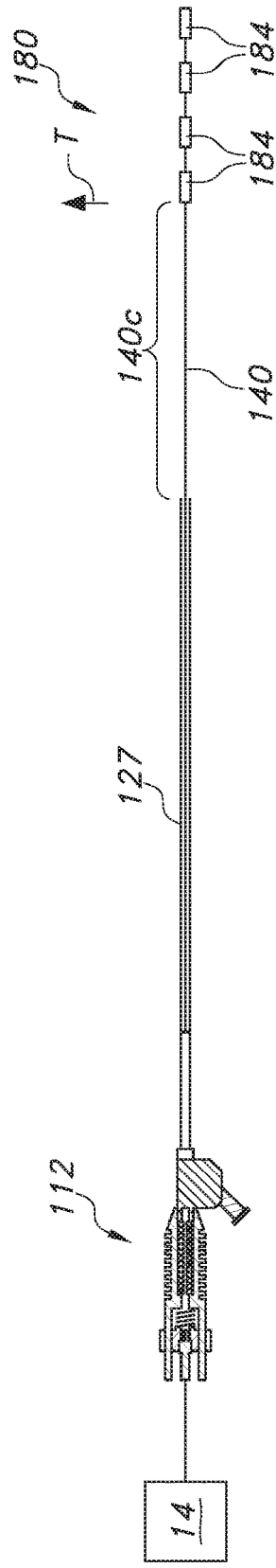
Figure 9:
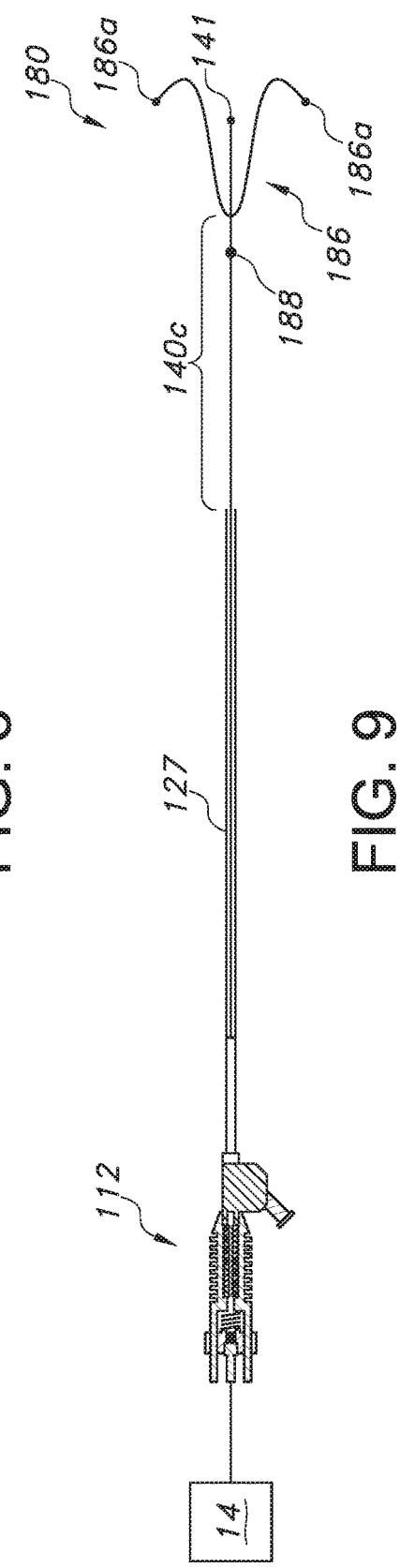
Figure 18:
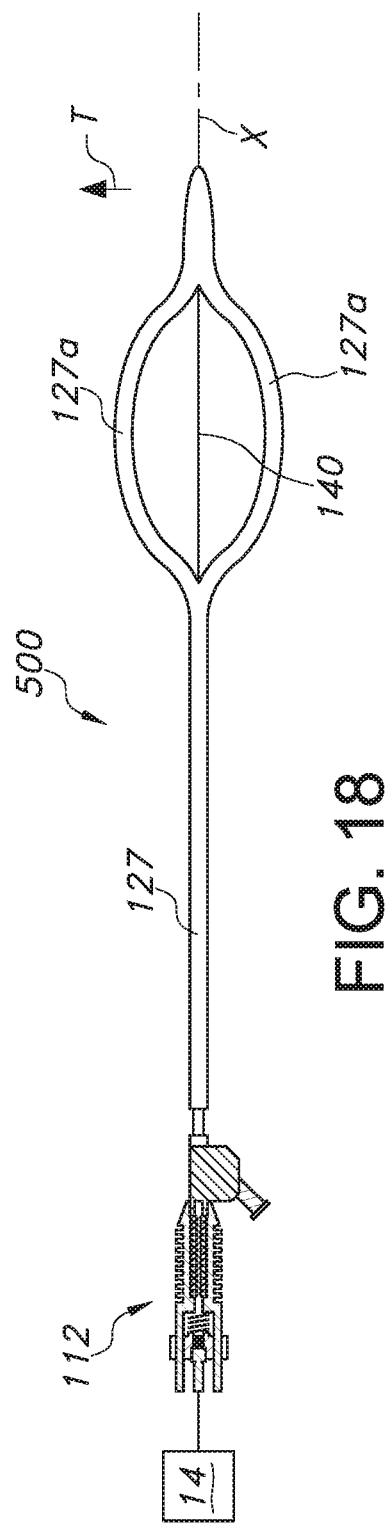

FIGS. 7, 8, and 9 are side views illustrating various anchors placed at a distal end portion of an ultrasonic wave guide;

FIGS. 10, 11, and 12 are side views of various filters placed at a distal end portion of an ultrasonic wave guide;

FIGS. 13, 14 and 15 illustrate an embodiment of an ultrasonic catheter including first and second inflatable balloons for isolating a treatment site to be treated by an exposed portion of a wave guide;

FIGS. 16 and 17 schematically illustrated another ultrasonic catheter including a tube that may transmit ultrasonic energy and also serve to inflate one or more associated balloons; and FIG. 18 illustrates still a further embodiment of an ultrasonic catheter including a plurality of curved portions spaced from a wave guide for transmitting energy to a treatment site.

Reference will now be made in detail to the presently disclosed embodiments of the inventive aspects of the ultrasonic endovascular catheter, examples of which are illustrated in the accompanying drawing figures.

DETAILED DESCRIPTION

Ultrasound or ultrasonic catheters provide for disruption of occlusions in blood vessels, such as for example, plaques, clots, lesions, or like objects that hinder blood flow. Catheters generally include a catheter body (shaft), an ultrasonic energy transmission member disposed within the catheter body and a distal head coupled with the energy transmission member and disposed at or near the distal end of the catheter body. The ultrasonic wave guide transmits ultrasonic energy from an ultrasonic transducer to the distal end of the catheter, causing it to vibrate and, thus, disrupt dissolve, or debulk vascular occlusions (which procedures are generally called atherectomies or thrombectomies). A number of improved features of such an ultrasonic catheter are outlined more fully in the following description.

Figure 1:
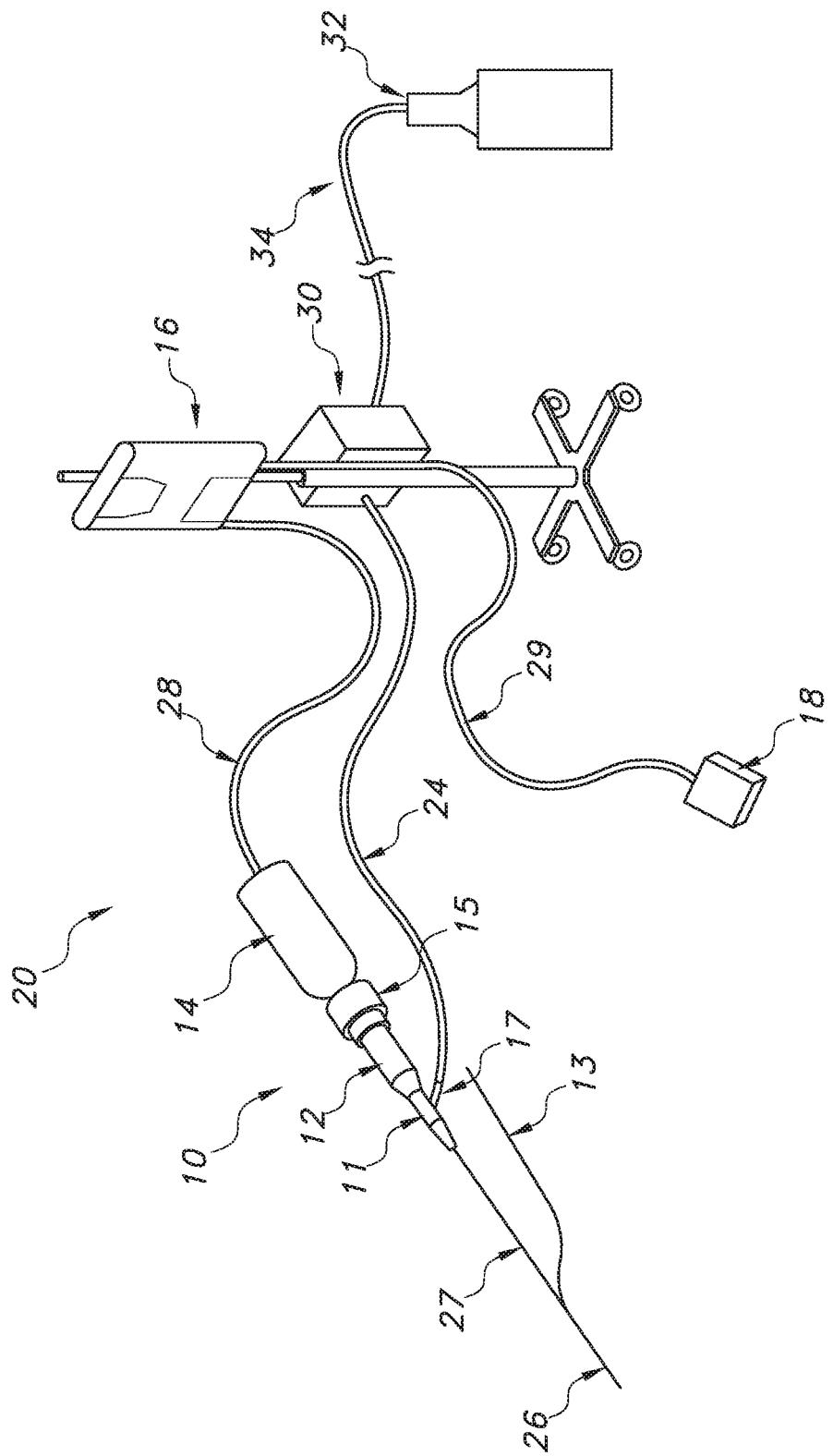
FIG. 1 is a schematic view of a prior art catheter system including an ultrasonic catheter.

Referring now to FIG. 1, one embodiment of an ultrasonic catheter system 20 includes an ultrasound or ultrasonic catheter 10 and an energy source 16 (which may comprise an ultrasonic generator). Catheter 10 includes a distal end 26 for disrupting occlusions, a catheter shaft or body 27, and a proximal connector 12 for coupling catheter 10 with an ultrasonic transducer 14. Ultrasonic transducer 14 is coupled with source 16 via a connector 28, and generator is coupled with a control, such as a foot-actuated on/off switch 18 via another connector 29. Source 16 provides energy to transducer 14 and, thus, to ultrasonic catheter 10.

Catheter 10 further includes an ultrasonic wave guide (or "core wire"—not shown in FIG. 1) that extends through the catheter body 27 and transmits energy from the transducer 14 to the distal end 26. Some embodiments of catheter 10 include a guidewire, which in FIG. 1 is shown as a so-called "rapid exchange" guidewire 13 and guidewire port, while other embodiments include a proximal guidewire port for over the wire guidewire delivery. In some embodiments, transducer 14 further includes a coupler 15 for coupling the catheter 10 to transducer 14. Connectors 28, 29 may comprise an electric cord or cable or any other suitable connecting devices for coupling on/off switch 18, source 16 and transducer 14. In an alternative embodiment, on/off switch 18 is located on source 16.

In addition to proximal connector 12, ultrasonic catheter 10 may include one or more other various components, such as a Y-connector 11 including a fluid inlet port 17 (or aperture) for passage of irrigation fluid. Inlet port 17 may be removably coupled with an irrigation tube 24, which in one embodiment may be coupled with a fluid refrigerator 30. The refrigerator 30 may, in turn, be coupled with a fluid container 32 via a connector tube 34. This arrangement may be used for introducing one or more fluids into catheter 10. Fluid may be used to cool any part of the device, such as the ultrasonic wave guide, thus helping reduce wear and tear on the catheter 10. In some embodiments, fluid inlet port 17 is located farther proximally on proximal connector 12, to allow fluid to be applied within connector 12. In some embodiments, refrigerated fluid is used, while in other embodiments irrigation fluid may be kept at room temperature. In various embodiments, oxygen supersaturated fluid, lubricious fluid, or any other suitable fluid or combination of fluids may be used, and again, such fluids may be refrigerated or kept room temperature. In an alternative embodiment to that shown in FIG. 1, refrigerator 30 and fluid container 32 are combined in one unit.

Generally, catheter 10 may include any suitable number of side-arms or ports for passage of a guidewire, application of suction, infusing and/or withdrawing irrigation fluid, dye and/or the like, or any other suitable ports or connections. Also, ultrasonic catheters 10 per the disclosure may be used with any suitable proximal devices, such as any suitable ultrasonic transducer 14, energy source 16, coupling device(s) and/or the like. Therefore, the exemplary embodiment shown in FIG. 1 and any following descriptions of proximal apparatus or systems for use with ultrasonic catheters 10 should not be interpreted to limit the scope of the appended claims.

Figure 2:
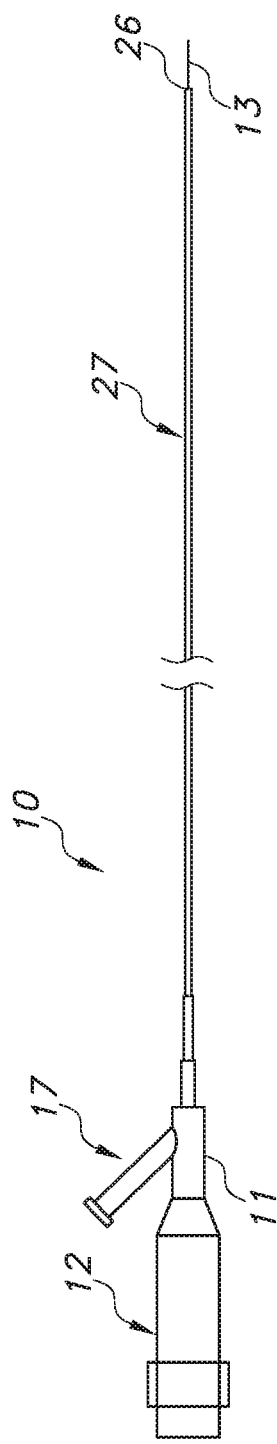
FIG. 2 is a side view illustrating a general layout of a prior art catheter.

Referring now to FIG. 2, an enlarged view of catheter 10 is shown. Proximal connector 12, Y-connector 11, inlet port 17, catheter body 27, distal end 26 and guidewire 13 are all shown. Catheter body 27 is generally a flexible, tubular, elongate member, having any suitable diameter and length for reaching a vascular occlusion for treatment. In one embodiment, for example, catheter body 27 preferably has an outer diameter of between about 0.5 mm and about 5.0 mm. In other embodiments, as in catheters intended for use in relatively small vessels, catheter body 27 may have an outer diameter of between about 0.25 mm and about 2.5 mm. Catheter body 27 may also have any suitable length. As discussed briefly above, for example, some ultrasonic catheters have a length in the range of about 150 cm. However, any other suitable length may be used without departing from the scope of the present disclosure.

Figure 3:
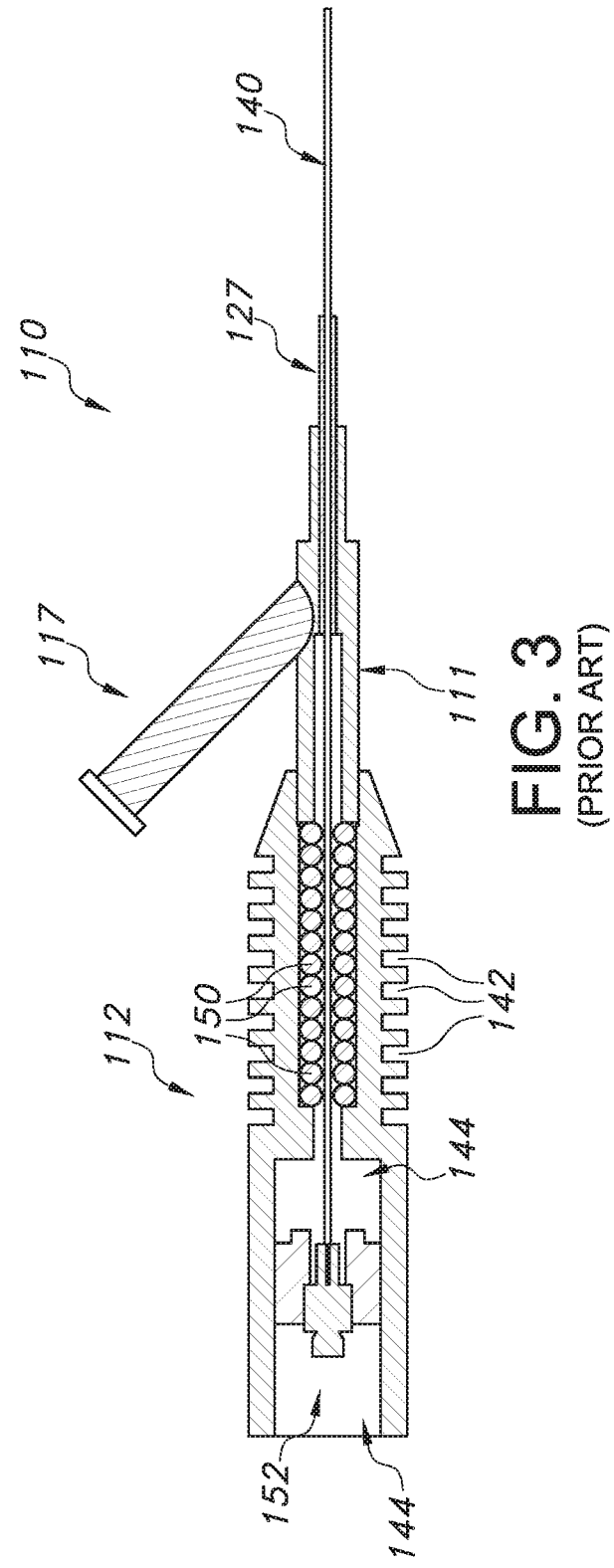
FIG. 3 is a partially cross-sectional, partially cutaway view of a catheter including an ultrasonic wave guide.

Referring now to FIG. 3, a proximal portion of one embodiment of an ultrasonic catheter 110 is shown in cross-section. An ultrasonic wave guide 140 extends from a sonic connector 152 distally to a distal end (not shown) of catheter 110. A catheter body 127 of catheter 110 is shown only in part, whereas catheter body typically extends distally to (or near) the distal end of catheter 110, with the wave guide 140 also extending a particularly long distance (e.g., 30 centimeters or greater, and typically between about 15 centimeters and 30 centimeters). The catheter body 127 may be a constant diameter, or may have a variable diameter from the proximal to the distal end (such as, for example, wider in diameter at the proximal end near the point of entering the vasculature than at the distal end, where the vessel is narrower)

Catheter 110 also includes a proximal housing 112 (or "proximal connector"), having an inner bore 144 (or "inner cavity") in which sonic connector 152, a portion of ultrasonic wave guide 140 and one or more vibration absorbers 150 reside. Housing 112 is coupled with a Y-connector 111, which includes a fluid inlet port 117 (or aperture), and Y-connector 111 is coupled with catheter body 127.

In various embodiments, housing 112 may suitably include one or more surface features 142 for increasing the overall surface area of the outer surface of housing 112. Increased surface area enhances the ability of housing 112 to dissipate heat generated by ultrasonic wave guide 140 out of catheter 110. Surface features 142 may have any suitable size or shape, such as ridges, jags, undulations, grooves or the like, and any suitable number of surface features 142 may be used. Additionally, housing 112 may be made of one or more heat dissipating materials, such as aluminum, stainless steel, any other conductive metal(s), or any suitable non-metallic conductive material(s).

In most embodiments, ultrasonic wave guide 140, such as wire, extends longitudinally through a lumen of catheter body 127 to transmit ultrasonic energy from an ultrasonic transducer 14 (not shown in FIGS. 2 and 3), connected to the proximal end of proximal housing 112, to the distal end of catheter 110. Wave guide 140 may be formed of any material capable of effectively transmitting ultrasonic energy from the ultrasonic transducer 14 to the distal end of catheter body 127, including but not limited to metals such as pure titanium or aluminum, titanium or aluminum alloys, or shape memory materials (such as nitinol), and may be coated (such as using a polymeric material). Again, additional details of ultrasonic wave guides 140 may be found in the patent applications incorporated by reference. Similarly, reference may be made to the incorporated patent applications for descriptions of housing 112, sonic connector 152, vibration absorbers 150, Y-connector 111 and the like. For example, housing 112 and other features are described in detail in Ser. No. 10/722,209, filed Nov. 24, 2003, entitled "Steerable Ultrasound Catheter," incorporated herein by reference.

Ultrasonic wave guide 140 typically passes from a sonic connector 152, through bore 144 and Y-connector 111, and then through catheter body 127. Fluid inlet port 117 is in fluid communication with a lumen in Y-connector, which is in fluid communication with a lumen extending through catheter body 127. Thus, fluid introduced into fluid inlet port 117 is typically free to flow into and through catheter body 127 to contact ultrasonic wave guide 140. Fluid may flow out of catheter body 127 through apertures in the distal head (not shown) or through any other suitable apertures or openings, such as apertures located in catheter body 127 itself. Any suitable fluid may be passed through fluid inlet port 117 and catheter body 127, such as refrigerated fluid, lubricious fluid, super-saturated saline or contrast/saline mixture, or the like. Cooling and/or lubricating ultrasonic wave guide 140 may reduce friction and/or wear and tear of ultrasonic wave guide 140, thus prolonging the useful life of ultrasonic catheter 110 and enhancing its performance.

Figure 4:
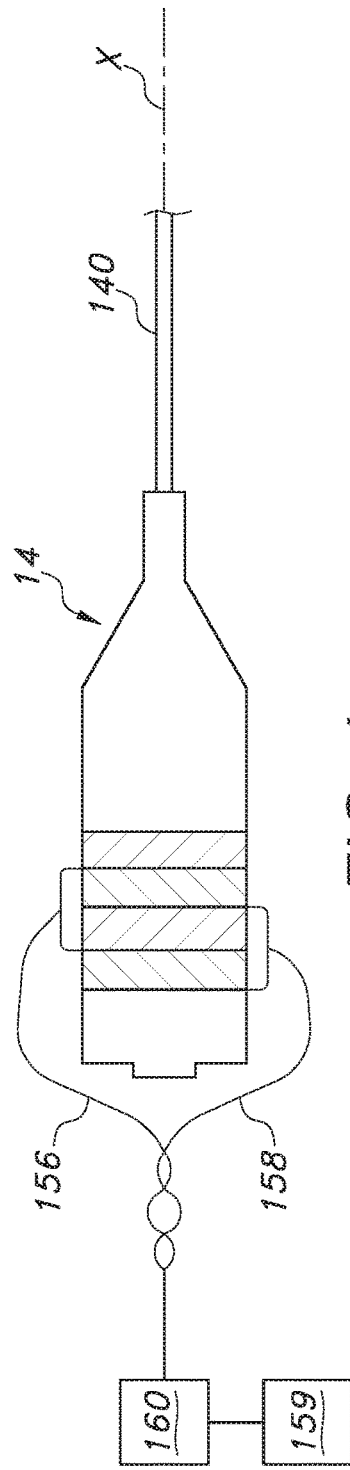
FIG. 4 is a partially cutaway, schematic view illustrating an actuator for both vibrating and rotating the wave guide.

Referring now to FIG. 4, the wave guide 140 or wire may employ an actuator that both vibrates the wave guide through the application of ultrasonic energy, such as from transducer 14, and also causes it to rotate about its longitudinal axis X, such as through the application for rotational motion to the transducer or any structure connected to the wave guide. In one embodiment, this may be achieved by providing an integral, rotary motor 154 as part of the ultrasonic transducer 14 (which may include the sonic connector 152 therein, or the wave guide 140 may be crimped directly onto the horn of the transducer). Power for the motor 154 may be supplied by a pair of wires 156, 158 (one to ground, one to positive) for causing relative rotation of the wave guide 140. Wires 156, 158 may be connected to an energy source, such as a power supply 160 for powering both the motor 154 and the transducer 14 (but separate sources could be used, including for example, integral batteries to avoid the need for external wires).

As illustrated, the wires 156, 158 if present may be twisted to allow for the relative rotation without creating binding problems. The rotation of the wave guide 140 may be continuous in one direction, or may be bi-directional (including a rotation of less than 360 degrees in each direction, such that the wave guide may be caused to oscillate about the longitudinal axis X). Control of the rotation may be provided by an associated controller 159 for controlling the power supply 160, which may reverse the flow of current to the motor 154 according to a preprogrammed operation or as a result of manual control provided by a clinician to control the relative direction and amount of rotation. Using the controller 159, the rotation may also be selectively turned on and off, while the vibratory energy is on, or the rotation may be provided while the vibratory energy is turned off.

Figure 5:
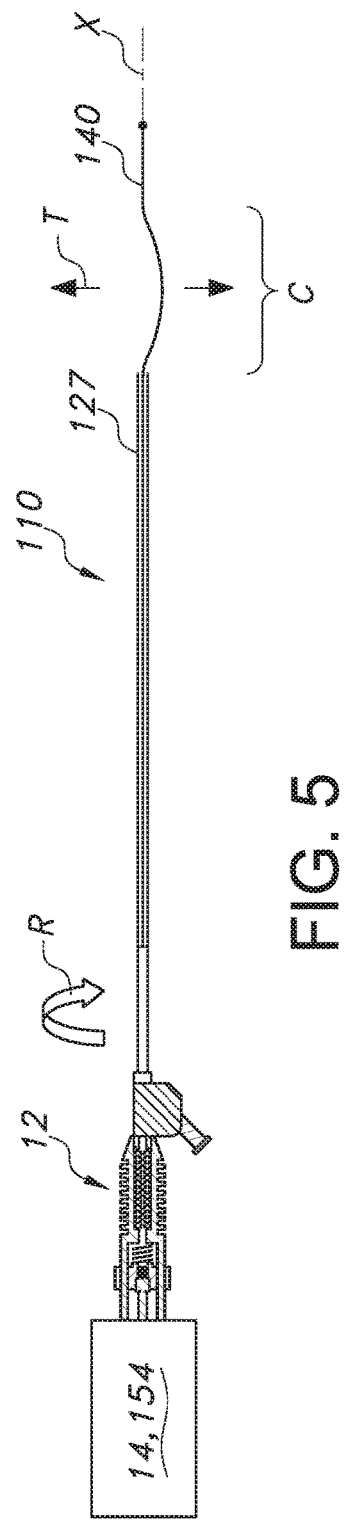
FIGS. 5 and 6 are views illustrating the wave guide including different curved portions for moving in the transverse direction to enhance the treatment provided in terms of dissolving an obstruction in a vessel receiving the wave guide.
Figure 6:
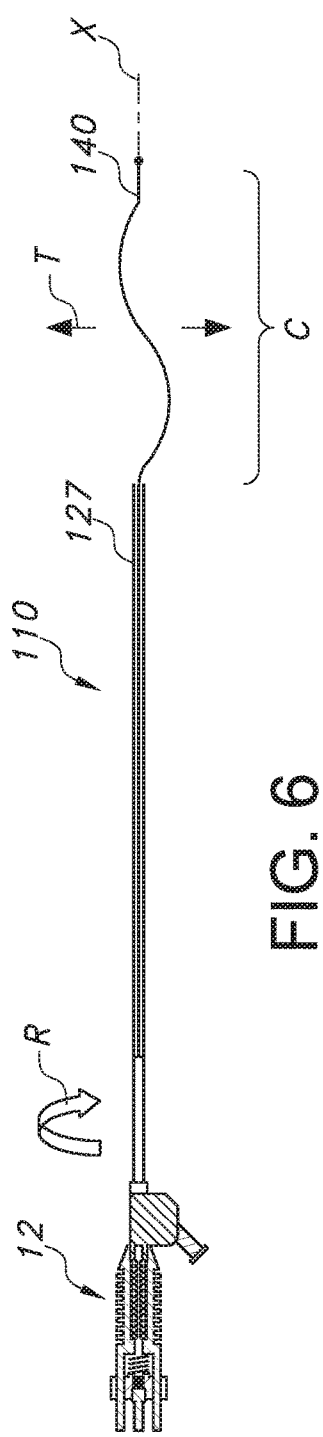

As indicated in FIGS. 5 and 6, the wave guide 140 may also be provided with a curved portion C, which may include a single curve (FIG. 5) or multiple curves (FIG. 6). The curved portions C extend in the transverse direction T and thus are spaced from the axis X. Thus, causing the wave guide 140 to rotate (arrow R) using motor 154 or otherwise rotating it via an imparted external force, creates movement in the transverse direction T. Combined with the vibration created by the ultrasonic energy transmitted from transducer 14, the wave guide 140 may thus serve to engage and clear an obstruction, such as a plaque, lesion or thrombus/embolus, when positioned in a blood vessel and associated with connector 112 of catheter 110. The catheter body 127 may also be advanced in the vessel and suction applied (such as through port 117) to aspirate any dislodged material (which may be done using a two part telescoping catheter body, such that one part remains connected to connector 112 and another part advances and retracts relative to the connected part).

Turning now to FIGS. 7-9, a further aspect of the disclosure is illustrated in several embodiments. In these embodiments, the wave guide 140 is provided with an anchor 180 at a distal end thereof, which may include a tip 141. This anchor serves to hold the distal end of the wave guide at a centered location within the vessel, and preclude it from moving in a transverse direction T.

In the FIG. 7 embodiment, the anchor 180 is shown as including a coil 182 having a radial extent that is substantially greater than the diameter of the wave guide 140 for engaging the interior walls of the blood vessel. The coil 182 may have a single loop or multiple loops, as shown. As noted above, the wave guide 140 may also be provided with an initially straight configuration (such as for passing into or through an obstruction, such as a thrombus), and as a result of a shape memory material, be caused to assume the coiled configuration in situ as a result of a temperature change (such as by a refrigerated fluid). The coil 182 may also have a conical configuration with a relatively tight coil, and may thus function as a filter for capturing any dislodged material during the endovascular procedure.

Alternatively or additionally, the FIG. 8 embodiment shows that the anchor 180 takes the form of one or more weights 184 positioned proximally of the tip 141. These weights 184 may be in the form of balls (which may be generally spherical), and thus serve to hold the distal end of the wave guide 140, and preclude it from moving in a transverse direction T. As illustrated, the tip 141 may also optionally comprise a weight 184. The extended length of section 140c may be controlled by advancing or retracting catheter body 127.

For the embodiment of FIG. 9, the anchor 180 comprises an anchoring cone 186, which may have circumferentially spaced radial extensions 186a for engaging the vessel walls to provide a centering function, and again transmitting the ultrasonic energy locally to the proximal portion 140c of the wave guide 140. As with the FIG. 7 embodiment, the cone 186 may also be provided with an initially relaxed configuration for insertion, and as a result of a shape memory material, be caused to assume the deployed configuration in situ as a result of a temperature change (such as by a refrigerated fluid).

This embodiment further illustrates that the cross-section of the wave guide 140 may be locally increased, such as by creating a spherical ball 188 therein. This helps to ensure that the wave guide 140 does not disconnect from the anchor 180 as a result of the foreshortening and lengthening creating during the application of vibratory energy. Multiple balls 188 may also be provided, such as one distal of the anchor 180 and one proximal of the anchor. The balls 188 may be generally spherical, and a distal ball provided at tip 141 may be made by melting the material of the wave guide 140.

Turning now to FIGS. 10, 11 and 12, it can also be appreciated that a distal end of the wave guide 140 may be provided with a filter 190, which may be initially collapsed for passing through a thrombus B in a vessel V via a soft tip 191. In the illustrated embodiment, the filter 190 when expanded (such as by using a shape memory material) includes an open proximal end 12 and a body 194 comprising a filtering material, such as a fine mesh, cage, or the like. Thus, when the wave guide 140 is ultrasonically vibrated, any particles loosened from the obstruction (e.g., thrombus B) as a result may travel distally through the open end of the filter 190 and be captured by the body 194 for later removal once the procedure is completed. To remove any captured particles or objects, the filter 190 may be collapsed, such as using an external sheath 193 (which may also provide suction via a provided port to withdraw any dislodged material).

FIGS. 11 and 12 illustrate a specific example of a filter 190, which may comprise a body 194 including an expandable frame 196 (again, using a shape memory material) supporting a flexible or foldable material 198, such as a fabric, film (such as, for example, a porous polymer film), or the like. The frame 196 when expanded may form a conical structure having an open proximal end 192 oriented similarly as in FIG. 10 and a closed distal end. The material 198 connected to the frame forms a basket for capturing dislodged particles created from the vibration of the wave guide 140. As illustrated, the filter 190 may be connected to the wave guide 140 by tethers 196a, which may also form part of the frame 196, and thus the wave guide may also transmit vibratory energy to the filter 190. To remove any captured particles or objects, the filter 190 may be collapsed, such as by using temperature control to return the shape memory material to its original state during insertion.

A further embodiment of an ultrasonic catheter 200 is illustrated with reference to FIGS. 13 and 14. In this embodiment, the catheter body 127 supports a plurality of inflatable balloons. Specifically, a first balloon 202 is positioned adjacent a distal end of the body 127, and a second balloon 204 is positioned proximally of the first balloon. The balloons 202, 204 may be inflated via a dual or coaxial inflation lumen 128 provided in the catheter body 127, which may include inlets 128a located in and communicating with the interior compartment of each balloon. Lumen 128 may receive inflation fluid from the fluid inlet port 117. When inflated, the balloons 202, 204 thus serve to anchor the catheter 200 at a treatment site, and also isolate a portion of the site for undergoing treatment.

The catheter body 127 may also include a second lumen 129 for receiving the wave guide 140. This second lumen 129 allows for an exposed portion to exit and pass external to the body 127 along a distal portion thereof, and ultimately re-enter the body at a point distal of the exit point, but proximal of the first distal balloon 202. To avoid interfering with the ultrasonic vibration of the wave guide 140, a corresponding portion 127a of the catheter body 127 may be non-linear or curved, and thus spaced from the wave guide 140, but could optionally be straight or partially curved.

A third lumen 130 in the body 127 may communicate with openings 130a in the portion 127a of the catheter body 127 intermediate the balloons 202, 204. These openings 130a may be used to withdraw fluid from a vessel when the body 127 is inserted therein, such as through a fluid port 118 associated with the connector 112. Alternatively, the openings 130a via lumen 130 or may be used to deliver substances to the vessel, such as, for instance, thrombolytic agents (such as, for example, Eminase (anistreplase) Retavase (reteplase) Streptase (streptokinase, kabikinase) t-PA (class of drugs that includes Activase) TNKase (tenecteplase) Abbokinase, Kinlytic (rokinase), or others). The body 127 may also optionally include a guidewire lumen 131 for receiving a guidewire 13, but use of a rapid-exchange configuration as described above is also possible.

In use, the wave guide 140 as a result of the advancement of the catheter body 127 may pass through or adjacent the obstruction in a vessel, such as thrombus B. The balloons 202, 204 may be inflated in the vessel being treated to concurrently anchor the catheter 200, which as can be appreciated serves to isolate a portion of the vessel including the obstruction (thrombus B). Substances such as thrombolytic agents may then be optionally delivered to the isolated portion of the vessel under treatment via port 118, lumen 130, and openings 130a to aid in dissolving the obstruction, and concurrently (or not), the wave guide 140 may be used to deliver ultrasonic energy to further assist in clearing the obstruction.

With the balloons 202, 204 remaining inflated, it can also be appreciated that the openings 130a may be used to remove material (including fluid) from the isolated portion of the vessel, such as by applying appropriate suction to the port 118. This may be done after a suitable amount of time has passed to ensure that any agents introduced have had time to act on the obstruction. When the obstruction is reduced or removed, the balloons 202, 204 may be deflated and the catheter body 127 moved along guidewire 13 as desired for removal or further treatment at an alternate location.

A further embodiment of an ultrasonic catheter 300 is shown in FIGS. 16 and 17, which includes a catheter body 127. In FIG. 16, the wave guide 140 comprises a tube 302, rather than a solid wire. This tube 302 which may be used to transmit ultrasonic energy from a transducer 14 to an obstruction, such as thrombus B (or thrombi). The distal end 302a of the tube 302 serving as wave guide 140 may be capped by an atraumatic tip 304, which may be used to move the tube 302 through the thrombus B (or thrombi). The tip 304 may also include a guidewire lumen 304a for guiding the tube 302 along a guide wire (not shown), which may be associated with a lumen in the catheter body 127 (see, e.g., FIG. 14).

In one particular embodiment, the tube 302 is adapted to inflate a balloon 306. The balloon 306 may be supported on the tube 302 proximally of the tip 304. The inflation fluid for inflating the balloon 306 may flow through the tube 302 via a proximal port (not shown). The fluid may exit the tube 302 to the interior compartment of the balloon via a port 302b.

In use, the catheter 300 may be partially passed through the obstruction (thrombus or thrombi) using tip 304 to extend the tube 302 therethrough, and the balloon 306 inflated. The transducer 14 may be activated to transmit energy to the obstruction to disrupt or dislodge it, with any dislodged particles or material being aspirated through the catheter body 127 (see arrows A). Additionally or alternatively, any thrombolytic agents may be delivered via the catheter body 127 to the treatment site prior to or during the tube activation to facilitate dissolving the obstruction, with any such substances remaining at the introduction site in view of the distal blockage created when the balloon 306 is inflated. When the procedure is complete, the balloon 306 may be deflated using the port 302b, and the catheter 300 moved accordingly.

FIG. 17 further illustrates that a second, proximal balloon 308 may also be provided on the ultrasonic catheter 300, which may likewise be inflated using a port 302c in tube 302 (such as using a coaxial or dual lumen). The balloons 306, 308 may thus be inflated on either side of the obstruction to isolate it. Wave guide 140 may be activated as desired to disrupt the obstruction. Ports or openings 302d may also be provided in the tube 302 for aspirating debris or introducing treatment agents, with corresponding lumens (not shown) provided in the tube as necessary for this purpose (see, e.g., multi-lumen catheter body 127 in FIG. 14). Alternatively, once the obstruction is cleared, the proximal balloon 308 may be deflated and the body 127 used to aspirate any dislodged material.

Turning now to FIG. 18, a further embodiment of an ultrasonic catheter 500 is shown. In this embodiment, the catheter body 127 may include one or more curved portions, such as two curved portions 127a, that are spaced in a transverse direction T from the wave guide 140. In the illustrated embodiment, the portions 127a are symmetrical about the longitudinal axis X and curved in opposition to each other (relative to a central longitudinal axis of the catheter). These portions 127 thus provide a centering function for the wave guide 140, which may be exposed in a space between the portions 127a for transmitting ultrasonic energy from an associated transducer 14 to a treatment site. The wave guide 140 may also extend to and possibly through a distal tip of the catheter body 127, and may be connected to it.

In summary, improved ultrasonic catheters 110, 200, 300, 500 are disclosed. In one example, the catheter 110 includes a wave guide 140 for transmitting ultrasonic energy from a transducer 14, and which is also rotated by a motor 154 to facilitate enhanced disruption of the concerned obstruction in a transverse direction. Embodiments of waveguide 140 include distal anchors 180 to restrain a corresponding portion of the waveguide, and may also include a deployable filter 190 that may open distal of the obstruction to capture any dislodged debris (which may be aspirated by the catheter body 127, including by advancing it). An embodiment of an ultrasonic catheter 200 is also disclosed that includes selectively inflatable balloons 206, 208 to cordon off a treatment site, as well as an embodiment in which the waveguide 104 comprises a tube 302 that may serve the dual purposes of inflating an associated balloon 306 (or balloons 306, 308), as well as to transmit ultrasonic energy to an obstruction. Still a further embodiment of a catheter 500 comprises a plurality of curved portions 127a spaced from a wave guide 140.

The foregoing description has been presented for purposes of illustration. It is not intended to be exhaustive or to limit the embodiments to the precise form disclosed. Obvious modifications and variations are possible in light of the above teachings. All modifications and variations are within the scope of the appended claims when interpreted in accordance with the breadth to which they are fairly, legally and equitably entitled.

What is claimed:

1. An apparatus for performing an endovascular procedure, comprising:
   a catheter body including a lumen extending along a proximal end portion and a distal end portion, the catheter body having at the distal end portion opposed portions, the proximal end portion being positioned along a central longitudinal axis;
   an ultrasonic wave guide including a first portion positioned within the lumen and a second exposed portion, wherein the opposed portions at the distal end portion of the catheter body are spaced directly across the central longitudinal axis and are spaced in a transverse direction from the central longitudinal axis, wherein a gap is defined between the opposed portions, the second exposed portion of the ultrasonic wave guide extends in the gap, each of the opposed portions has an entire length, the opposed portions are reflectively symmetrical about the central longitudinal axis, each opposed portion curves along the central longitudinal axis along the entire length, and wherein the opposed portions provide a centering function for the ultrasonic wave guide at a treatment site; and
   an ultrasonic transducer coupled to the ultrasonic wave guide for vibrating the ultrasonic wave guide at an ultrasonic frequency.

2. An apparatus for performing an endovascular procedure, comprising:
   an ultrasonic catheter positioned along a central longitudinal axis, the ultrasonic catheter including a proximal end portion, the proximal end portion including a lumen, and the ultrasonic catheter including opposed portions distal to the proximal end portion, wherein the opposed portions are spaced in a transverse direction from the central longitudinal axis, wherein the opposed portions define a transverse gap; and an ultrasonic wave guide including a first portion positioned within the lumen and a second exposed portion, the ultrasonic wave guide being positioned along the central longitudinal axis, the second exposed portion being exposed in the transverse gap between the opposed portions of the ultrasonic catheter, the second exposed portion extending in the transverse gap between the opposed portions of the ultrasonic catheter, wherein the opposed portions are reflectively symmetrical about the central longitudinal axis, the opposed portions curve along the central longitudinal axis, and wherein the opposed portions provide a centering function for the ultrasonic wave guide at a treatment site.

3. The apparatus of claim 2, further including an actuator having an ultrasonic transducer coupled to the ultrasonic wave guide for vibrating the ultrasonic wave guide at an ultrasonic frequency.

4. The apparatus of claim 2, wherein the opposed portions curve along the central longitudinal axis of the ultrasonic catheter in opposite directions to define the transverse gap.

5. The apparatus of claim 2, wherein an ultrasonic catheter further includes a distal tip through which the ultrasonic wave guide extends.

6. The apparatus of claim 2, wherein an ultrasonic catheter further includes a distal tip, wherein the ultrasonic wave guide extends to the distal tip.

7. The apparatus of claim 2, wherein an ultrasonic catheter further includes a distal tip, wherein the ultrasonic wave guide is connected to the distal tip of the ultrasonic catheter.

8. An apparatus for performing an endovascular procedure, comprising:

a catheter body including a lumen extending along a proximal end portion and a distal end portion, the proximal end portion being positioned along a central longitudinal axis, the catheter body having at the distal end portion opposed portions that curve along the central longitudinal axis, the opposed portions comprise a first opposed portion and a second opposed portion, the first opposed portion is spaced across the central longitudinal axis from the second opposed portion, the opposed portions defining a space between;

an ultrasonic wave guide including a first portion positioned within the lumen and a second exposed portion, the second exposed portion extending through the space, the ultrasonic wave guide having a total length, wherein the second exposed portion has a second exposed portion entire length, the total length of the ultrasonic wave guide is positioned along the central longitudinal axis, wherein the opposed portions provide a centering function for the ultrasonic wave guide at a treatment site; and an ultrasonic transducer coupled to the ultrasonic wave guide for vibrating the ultrasonic wave guide at an ultrasonic frequency, wherein the opposed portions are reflectively symmetrical about the central longitudinal axis for an entirety of the second exposed portion entire length.

* * * * *